(12) United States Patent
O'Connor et al.

(10) Patent No.: US 7,918,825 B2
(45) Date of Patent: Apr. 5, 2011

(54) INTERFACING A PREFILLED SYRINGE WITH AN INFUSION PUMP TO FILL THE INFUSION PUMP

(75) Inventors: Jason Brian O'Connor, South Boston, MA (US); Luis Malave, Reading, MA (US)

(73) Assignee: Insulet Corporation, Bedford, MA (US)

( * ) Notice: Subject to any disclaimer, the term of this patent is extended or adjusted under 35 U.S.C. 154(b) by 222 days.

(21) Appl. No.: 11/947,117

(22) Filed: Nov. 29, 2007

(65) Prior Publication Data

US 2009/0143732 A1 Jun. 4, 2009

(51) Int. Cl.
*A61M 1/00* (2006.01)
(52) U.S. Cl. .................. 604/151; 604/890.1; 604/28
(58) Field of Classification Search .................. 604/181, 604/411–415, 890.1–892.1, 256
See application file for complete search history.

(56) References Cited

U.S. PATENT DOCUMENTS

| 5,876,377 | A | * | 3/1999 | Kriesel | .......................... 604/133 |
| 7,220,245 | B2 | | 5/2007 | Kriesel | |
| 2005/0238507 | A1 | | 10/2005 | DiIanni | |
| 2006/0282290 | A1 | | 12/2006 | Flaherty | |
| 2008/0051765 | A1 | * | 2/2008 | Mounce | ...................... 604/890.1 |

OTHER PUBLICATIONS

International Search Report and Written Opinion dated Feb. 13, 2009 issued in related International Patent Application No. PCT/US08/84971.
NovoLog, "NovoLog Flex Pen," available at http://www.novolog.com/devices-flexpen.asp; retrieved on Sep. 11, 2007.

* cited by examiner

*Primary Examiner* — Nicholas D Lucchesi
*Assistant Examiner* — Leah Stohr
(74) *Attorney, Agent, or Firm* — Grossman Tucker Perreault & Pfleger, PLLC (57) ABSTRACT

A prefilled syringe may be interfaced with and used to fill an infusion pump with therapeutic liquid. The dispensing end of the prefilled syringe may be coupled (either directly or indirectly using a syringe cap) to a syringe coupling region of the infusion pump, for example, using a threaded engagement or snap fit engagement. As the dispensing end of the prefilled syringe is coupled to the syringe coupling region of the pump housing, a needle passes through the pump housing and/or a needle passage region of the dispensing end such that the prefilled syringe is fluidly coupled to a reservoir in the pump. In various embodiments, the needle may be located in the syringe coupling region or in a syringe cap coupled to the dispensing end of the prefilled syringe.

5 Claims, 6 Drawing Sheets

INTERFACING A PREFILLED SYRINGE WITH AN INFUSION PUMP TO FILL THE INFUSION PUMP

TECHNICAL FIELD

The present invention relates to infusion pumps for delivering therapeutic liquids to a patient and more particularly, to interfacing a prefilled syringe with an infusion pump.

BACKGROUND INFORMATION

Fluid delivery devices have numerous uses such as delivering a therapeutic liquid (e.g., a liquid medicine) to a patient subcutaneously. In a patient with diabetes mellitus, for example, ambulatory infusion pumps have been used to deliver insulin to a patient. These ambulatory infusion pumps have the ability to offer sophisticated fluid delivery profiles including variable basal rates and bolus requirements. The ability to carefully control drug delivery can result in better efficacy of the drug and therapy and less toxicity to the patient.

Some existing ambulatory infusion pumps include a reservoir to contain the liquid medicine and use electromechanical pumping or metering technology to deliver the therapeutic liquid to a needle and/or soft cannula that is inserted subcutaneously into the patient. The infusion pumps are generally provided with an empty reservoir, which must be filled with the therapeutic liquid. Using conventional techniques, the reservoir may be filled by first filling a syringe with the therapeutic liquid and then injecting the liquid into the reservoir via a fill port in the pump. The process of filling the syringe typically involves numerous steps such as sterilizing the vial of insulin, injecting the syringe needle, retracting the syringe plunger and removing air from the syringe. Also, the exposed needle of such syringes may be hazardous and requires additional care when filling the pump.

Existing prefilled syringes, such as syringe "pens," may be obtained already filled with therapeutic liquid. The process of filling the infusion pump would be simplified by using such a prefilled syringe; however, existing infusion pumps are not designed to interface with existing prefilled syringes. Without a proper interface to a prefilled syringe, the infusion pump may not be properly filled with the therapeutic liquid and the exposed needle of the prefilled syringe may be hazardous.

BRIEF DESCRIPTION OF THE DRAWINGS

These and other features and advantages will be better understood by reading the following detailed description, taken together with the drawings wherein.

DETAILED DESCRIPTION

Figure 1:
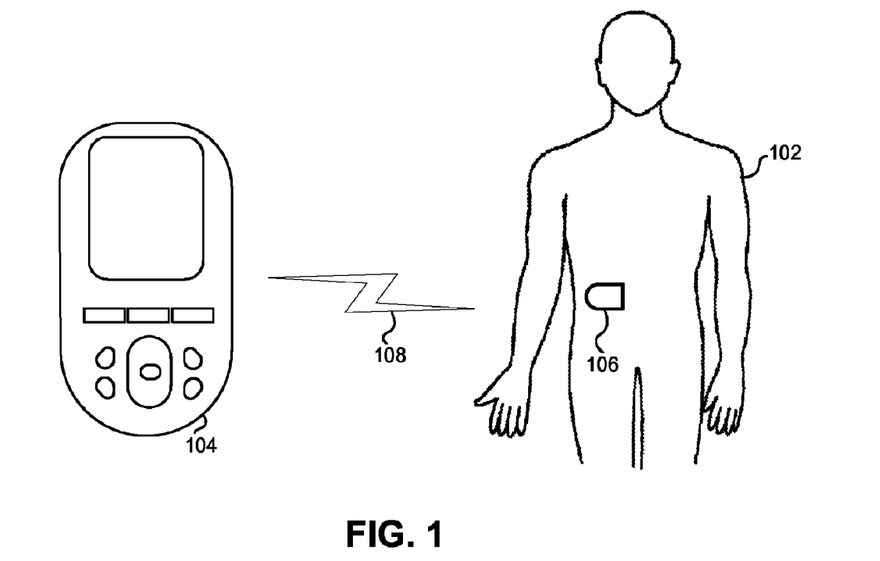
FIG. 1 is a diagrammatic view of a fluid delivery system including an infusion pump that may be filled with a therapeutic liquid, consistent with an embodiment of the present invention.

Consistent with embodiments of the present invention, a prefilled syringe may be interfaced with and used to fill an infusion pump with therapeutic liquid, as will be described in greater detail below. Referring to FIG. 1, one embodiment of a fluid delivery system 100 for delivering therapeutic liquid may include a hand-held delivery management device 104 and an infusion pump 106 worn by the patient 102. In the exemplary embodiments, the delivery management device 104 communicates with the infusion pump 106, for example, over a wireless communication link 108, to program and monitor the infusion pump 106 and to manage delivery of a fluid, such as insulin, to a patient according to a treatment regimen. One example of such a management device 104 and infusion pump 106 is the OmniPod® insulin management system available from Insulet Corporation. A prefilled syringe may also be interfaced with and used to fill other types of infusion pumps, such as a programmable infusion pump that integrates the management device and the infusion pump.

Figure 2A:
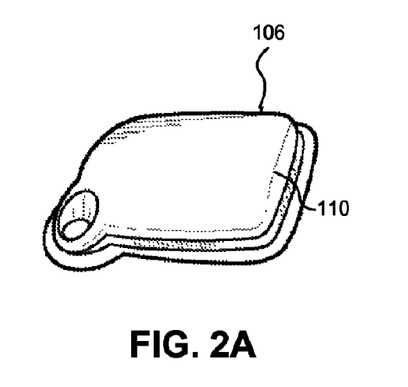
FIGS. 2A and 2B are top and bottom perspective views, respectively, of an infusion pump that may be filled with a therapeutic liquid, consistent with an embodiment of the present invention.
Figure 2B:
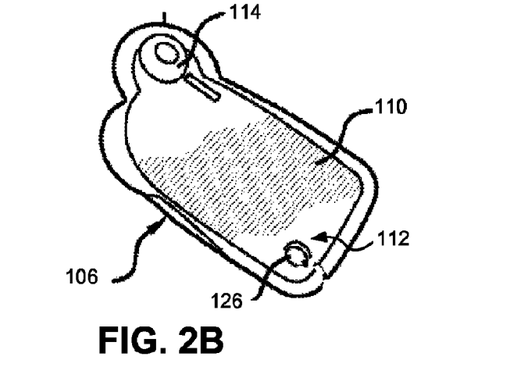
Figure 2C:
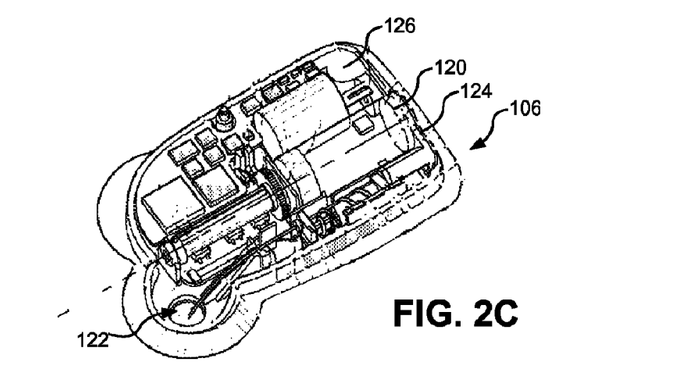
FIG. 2C is a top view of the fluid delivery components in the infusion pump shown in FIGS. 2A and 2B.

Referring to FIGS. 2A-2C, one embodiment of the infusion pump 106 is shown in greater detail. The infusion pump 106 generally includes fluid delivery components located in a pump housing 110. The fluid delivery components may include a reservoir 120 for receiving and holding fluid to be delivered by the pump 106, a transcutaneous access tool 122 (e.g., a needle/cannula) for providing fluid communication between the reservoir 120 and a patient, and a flow path assembly 124 connecting a fill port 126 to the reservoir 120 and the reservoir 120 to the transcutaneous access tool 122. The pump housing 110 may include a syringe coupling region 112 to couple a prefilled syringe to the fill port 126 and a transcutaneous access region 114 through which the transcutaneous access tool 122 extends. Other components include mechanisms for operating the transcutaneous access tool 120, mechanisms for causing fluid delivery from the reservoir 120, and electronic controls. Examples of infusion pumps are described in greater detail in U.S. Patent Application Publication Nos. 2005/0238507 and 2006/0282290, both of which are fully incorporated herein by reference.

The infusion pump 106 can be used for the delivery of therapeutic liquids to a person or animal. The types of liquids that can be delivered by the infusion pump 106 include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the infusion pump 106 might be used to treat include, but are not limited to, diabetes, cardiovascular disease, pain, chronic pain, cancer, AIDS, neurological diseases, Alzheimer's Disease, ALS, Hepatitis, Parkinson's Disease or spasticity. The volume of the reservoir 120 is chosen to best suit the therapeutic application of the infusion pump 106 impacted by such factors as available concentrations of therapeutic liquids to be delivered, acceptable times between refills or disposal of the infusion pump 106, size constraints and other factors.

Figure 3A:
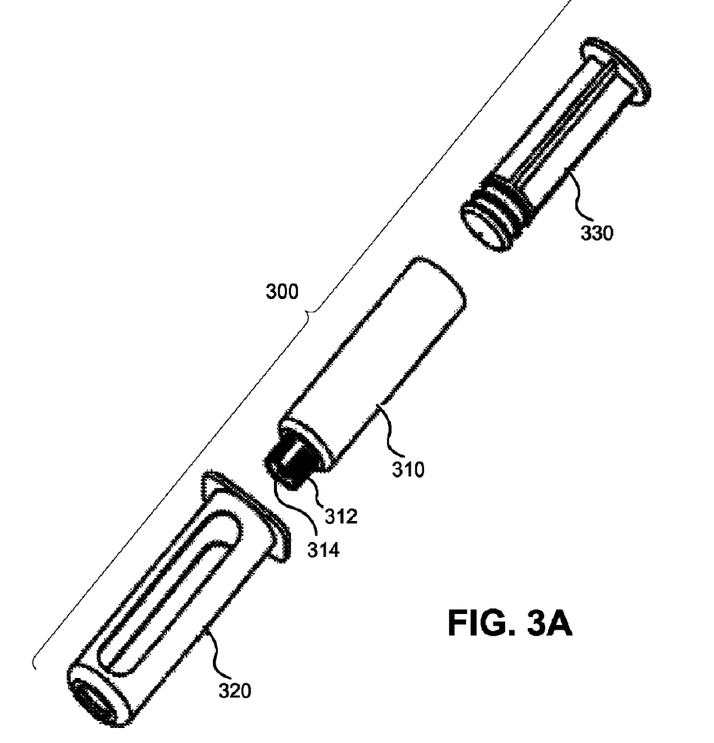
FIG. 3A is an exploded view of a prefilled syringe that may be used to fill an infusion pump, consistent with an embodiment of the present invention.
Figure 3B:
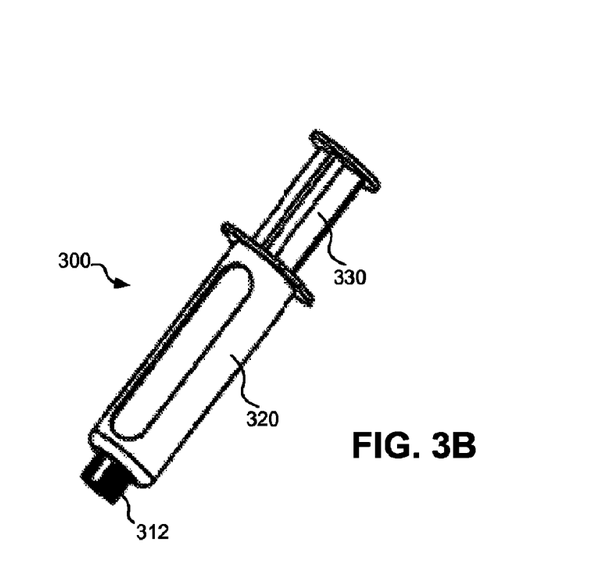
FIG. 3B is a side view of the assembled prefilled syringe shown in FIG. 3A.

One embodiment of a prefilled syringe 300 that may be used to fill an infusion pump is shown in FIGS. 3A and 3B. The prefilled syringe 300 may include a disposable prefilled vial 310, a syringe base 320 and a syringe plunger 330. The prefilled vial 310 includes a dispensing end 312 including a needle passage region 314, such as a valve or septum, capable of allowing a needle to pass through. The dispensing end 312 may be coupled to an infusion pump, either directly or indirectly using a syringe cap, as will be described in greater detail below. One embodiment of the dispensing end 312 is externally threaded to threadably engage an infusion pump or a syringe cap. The prefilled syringe 300 is prefilled with therapeutic liquid (e.g., insulin) and allows the user to set a predetermined amount of liquid to be delivered from the prefilled syringe 300 by pushing the syringe plunger 330 into the vial 310. One example of a prefilled syringe that may be used with embodiments of the present invention is the prefilled syringe available from Novo Nordisk Inc. under the name NovoLog® FlexPen®.

To fill an infusion pump, such as the infusion pump 106 described above, a prefilled syringe, such as the prefilled syringe 300, is coupled to the infusion pump 106. In particular, the dispensing end 312 of the prefilled vial 310 is coupled (either directly or indirectly using a syringe cap) to the syringe coupling region 112 of the infusion pump 106, for example, using a threaded engagement or snap fit engagement. As the dispensing end 312 of the prefilled vial 310 is coupled to the syringe coupling region 112 of the pump housing 110, a needle passes through the pump housing 110 and/or the needle passage region 314 of the dispensing end 312 such that the prefilled vial 310 is fluidly coupled to the reservoir 120 in the pump housing 110 via the fill port 126. As will be described in greater detail below, the needle may be located in the syringe coupling region 112 or in a syringe cap coupled to the dispensing end 312 of the prefilled vial 310 to avoid user exposure to the sharp tip(s) of the needle.

When the dispensing end 312 is coupled to the pump housing 110, a predetermined amount of the therapeutic liquid is dispensed from the prefilled vial 310 into the reservoir 120. By mechanically coupling the dispensing end 312 to the pump housing 110 (as opposed to merely being coupled by the needle), the prefilled syringe 300 is held more securely to ensure proper filling. When the predetermined amount has been dispensed into the reservoir 120, the dispensing end 312 is uncoupled or removed from the syringe coupling region 112. The prefilled syringe 300 may be reused until the prefilled syringe 300 is empty, and the user may then dispose of the prefilled syringe. The use of the prefilled syringe 300 thus facilitates filling of an infusion pump by eliminating the steps of having to first fill the syringe using the conventional techniques of filling a syringe by drawing liquid in through the needle.

Referring to FIGS. 4A-4D, one embodiment of an interface between a prefilled syringe 300 and a pump housing base 410 is shown and described in greater detail. According to this embodiment, a syringe cap 420 is used to provide the interface between the prefilled syringe 300 and the pump housing base 410. The syringe cap 420 includes a needle 428 that is coupled to the dispensing end 312 of the syringe 300 and to a syringe coupling region 412 on the housing base 410 to provide the fluid communication. The needle 428 may be a hollow needle capable of allowing the therapeutic liquid to pass through.

Figure 4A:
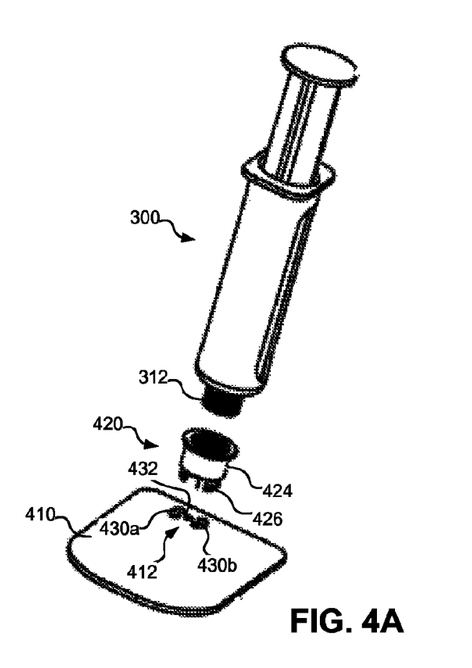
FIG. 4A is an exploded view of one embodiment of an interface between a prefilled syringe and an infusion pump.
Figure 4B:
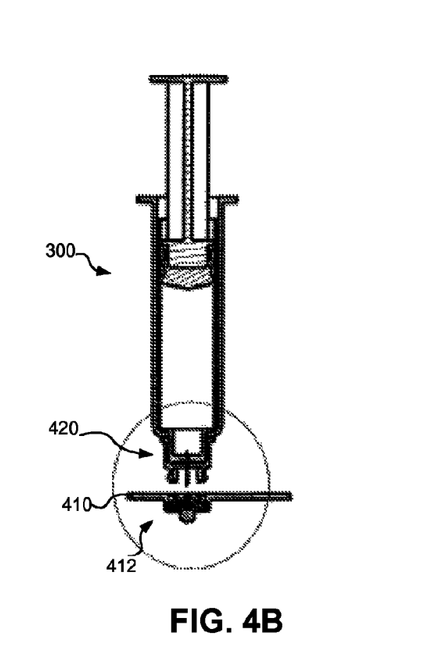
FIG. 4B is a side cross-sectional view of the interface shown in FIG. 4A.
Figure 4C:
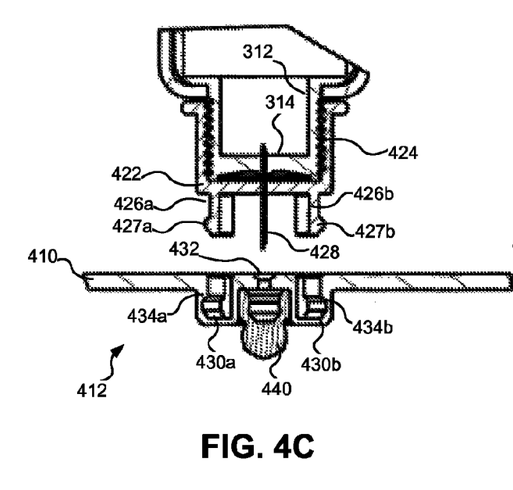
FIG. 4C is an expanded cross-sectional view of the interface shown in FIG. 4B.
Figure 4D:
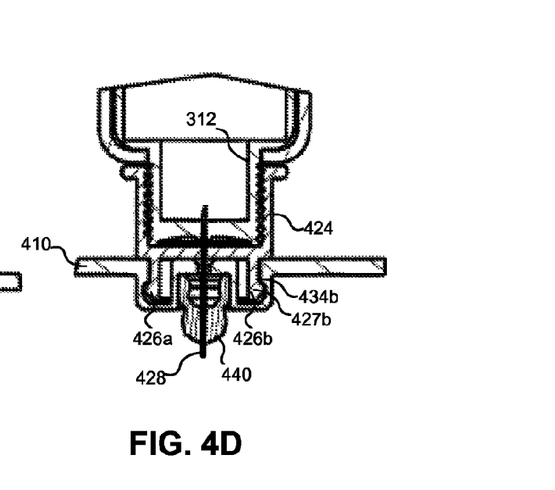
FIG. 4D is an expanded cross-sectional view of the interface shown in FIG. 4B with the prefilled syringe coupled to the pump.

According to this embodiment, the syringe coupling region 412 includes one or more recessed engaging portions 430*a*, 430*b* and a fill port 432 (FIGS. 4C and 4D). A septum 440 may cover and seal the fill port 432, for example, inside of the pump housing base 410. The septum 440 may include any device or piece of material, such as a silicone or other resealing elastomer, capable of sealing the fill port 432, allowing a needle 428 to pass through, and resealing when a needle 428 is withdrawn. In the illustrated embodiment, the septum 440 is positioned between the recessed engaging portions 430*a*, 430*b*, although other configurations are possible.

One embodiment of the syringe cap 420 includes a body portion 422, a syringe coupling portion 424 extending from one side of the body portion 422, and one or more base engaging members 426*a*, 426*b* extending from the other side of the body portion 422. The needle 428 passes through and is secured to the body portion 422 such that a first portion of the needle 428 extends on one side of the body portion 422 with the syringe coupling portion 424 and a second portion of the needle 428 extends on the other side of the body portion 422 with the base engaging member(s) 426*a*, 426*b*. The syringe coupling portion 424 and the base engaging member(s) 426*a*, 426*b* may thus provide at least some protection against "needle sticks." The needle 428 may also be surrounded on either end by a needle shroud (not shown), for example, made of a low durometer silicone The needle 428 is positioned relative to the syringe coupling member 424 such that the first portion of the needle 428 passes through the needle passage region 314 in the dispensing end 312 as the syringe coupling portion 424 engages the dispensing end 312 of the syringe 300 (FIG. 4C). The needle 428 is positioned relative to the base engaging member(s) 426*a*, 426*b* such that the second portion of the needle 428 passes through the fill port 432 and the septum 440 as the base engaging member(s) 426*a*, 426*b* engages the recessed engaging portion(s) 430*a*, 430*b* (FIG. 4D). In an exemplary embodiment, the septum 440 is compressed in the assembly and the needle 428 passes through the compressed septum 440 to provide fluid communication.

One embodiment of the syringe coupling portion 424 includes internal threads for engaging external threads on the dispensing end 312 of the syringe 300 in a threaded engagement. Thus, the needle 428 pierces the needle passage region 314 as the syringe cap 420 is threaded onto the syringe 300. Other types of mechanical coupling engagements may also be used between the syringe coupling portion 424 and the dispensing end 312, such as a snap fit engagement. In other embodiments, the syringe cap 420 may be integral or one-piece with the dispensing end 312 of the prefilled syringe 300.

One embodiment of the base engaging member(s) 426a, 426b includes cantilevered engaging members having raised portions 427a, 427b configured to engage lips 434a, 434b within the recessed engaging portions 430a, 430b in a snap fit engagement. Thus, the needle 428 pierces the septum 440 as the syringe cap 420 engages the syringe coupling portion 412 in a snap fit. Other types of mechanical coupling engagements may also be used between the base engaging member(s) 426a, 426b and the recessed engaging portion(s) 430a, 430b, such as a threaded engagement. Thus, when the prefilled syringe 300 is coupled to the pump housing base 410 using the syringe cap 420, the prefilled syringe 300 is held securely to ensure proper filling.

Referring to FIGS. 5A-5D, another embodiment of an interface between a prefilled syringe 300 and a pump housing base 510 is shown and described in greater detail. According to this embodiment, the dispensing end 312 of the prefilled syringe 300 is directly coupled to a syringe coupling region 512 on the pump housing base 510 (i.e., without using a syringe cap). The syringe coupling region 512 includes a needle 524 recessed behind the base 510 that passes into the needle passage region 314 as the dispensing end 312 is coupled to provide the fluid communication.

The syringe coupling region 512 includes a recessed engaging portion 520 that receives and engages the dispensing end 312 and provides a fill port 522. The needle 524 may be located in the recessed engaging portion 520 passing through the fill port 522. The needle 524 may be positioned within the recessed engaging portion 520 such that the needle 524 passes through the needle passage region 314 as the dispensing end 312 is engaged with the recessed engaging portion 520.

One embodiment of the recessed engaging portion 520 may be formed by a wall portion 526 extending from the housing base 510 (e.g., as one piece) and an end cap 528 that engages the wall portion 526 (e.g., in a snap fit). The wall portion 526 may include internal threads capable of engaging the dispensing end 312 in a threaded engagement. Other types of mechanical coupling engagements may also be used between the recessed engaging portion 520 and the dispensing end 312, such as a snap fit engagement. The fill port 522 and the needle 524 may be located in and secured to, respectively, the end cap 528. A transfer tube 529 may also be coupled to the needle 524 and may extend from the engaging portion 520 (e.g., molded with or coupled to the end cap 528) to transfer the therapeutic liquid from the needle 524 to a reservoir or to a passageway leading to a reservoir.

Figure 5A:
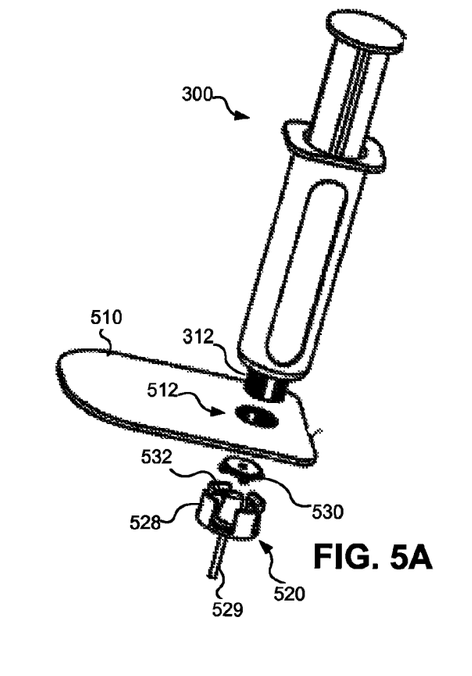
FIG. 5A is an exploded view of another embodiment of an interface between a prefilled syringe and an infusion pump.
Figure 5B:
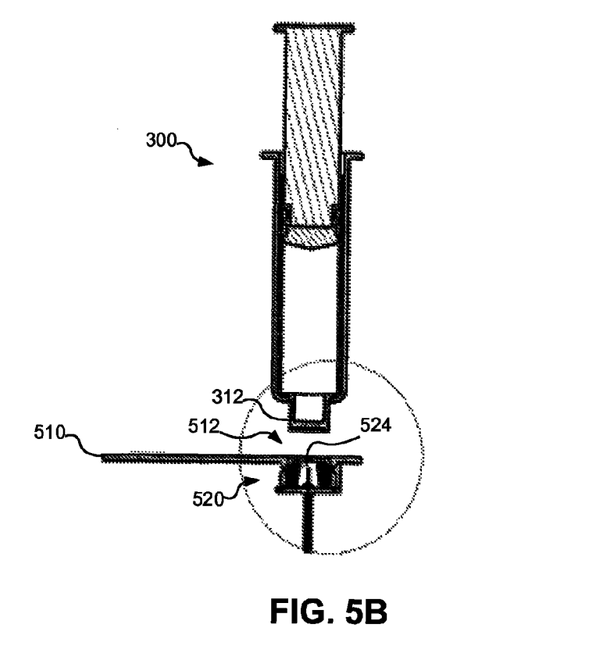
FIG. 5B is a side cross-sectional view of the interface shown in FIG. 5A.
Figure 5C:
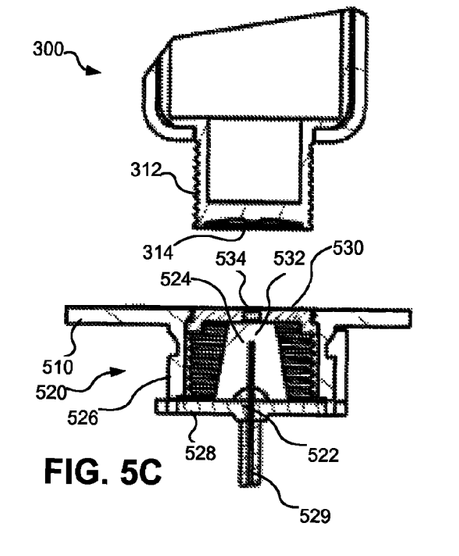
FIG. 5C is an expanded cross-sectional view of the interface shown in FIG. 5B.
Figure 5D:
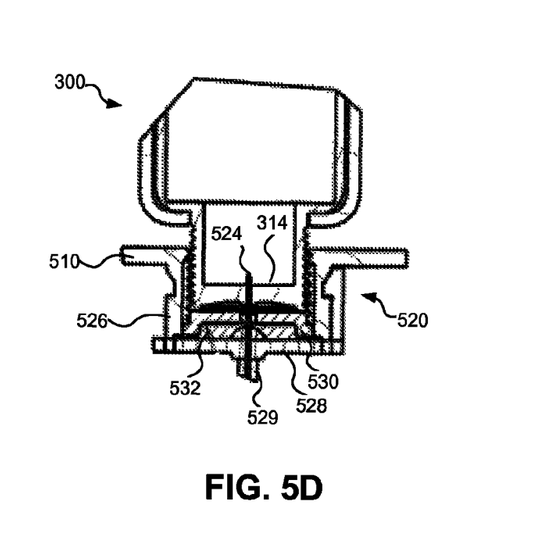
FIG. 5D is an expanded cross-sectional view of the interface shown in FIG. 5B with the prefilled syringe coupled to the pump.

According to one embodiment, a protective cover 530 and a needle shroud 532 may be positioned in the syringe coupling region 512 to protect the needle 524. The protective cover 530 is configured to fit within the recessed engaging portion 520 and to engage the dispensing end 312 such that protective cover 530 moves form a first position covering the needle 528 (FIG. 5C) to a second position exposing the needle (FIG. 5D). The protective cover 530 may include a hole 534 capable of receiving the needle 524 as the cover 530 is moved from the first position to the second position. Thus, providing the needle recessed in the recessed engaging portion 520 with the protective cover 530 and/or shroud 532 avoids user exposure to the sharp tip of the needle.

The needle shroud 532 may be positioned around the needle 524 and may be made of a pliable material that allows needle shroud 532 to compress around the needle 524. One example of such a pliable material is a low durometer silicone (e.g., having a durometer less than about 20 Shore A). The shroud 532 also functions as a seal to the fluid path. When the prefilled syringe 300 is removed, for example, the shroud 532 moves back over the needle 524 to create the fluid path seal. The protective cover 530 is positioned above the needle shroud 532 in the first position (FIG. 5C) and causes the needle shroud 532 to compress when moved to the second position (FIG. 5D). In one embodiment, the end cap 528 and needle shroud 532 may be formed together using a two shot molding process with the end cap 528 made of a polycarbonate or other suitable material and the needle shroud 532 made of silicone or other suitable material.

Referring to FIGS. 6A-6F, a further embodiment of an interface between a prefilled syringe 300 and a pump housing base 610 is shown and described in greater detail. In general, this embodiment of the interface causes a needle to move axially and advance into the dispensing end 312 of the prefilled syringe 300 in response to moving the prefilled syringe 300 into engagement with a syringe coupling region 612.

According to one embodiment, a syringe cap 620 coupled to the dispensing end 312 engages the syringe coupling region 612. One embodiment of the syringe cap 620 includes a syringe coupling portion 624 and one or more actuating members 622a, 622b extending from the syringe coupling portion 624. The syringe coupling portion 624 may be internally threaded to engage the dispensing end 312 of the prefilled syringe 300 in a threaded engagement. Other types of mechanical coupling engagements may also be used between the syringe coupling portion 624 and the dispensing end 312, such as a snap fit engagement. The pump housing base 610 may include one or more slots 614a, 614b (FIG. 6D) that receive the actuating member(s) 622a, 622b when the syringe cap 620 is engaged with the syringe coupling region 612.

According to one embodiment, a needle carrier 630 is located in a recessed portion 640 in the syringe coupling region 612. The needle carrier 630 may include a disc-shaped body portion 634 that secures a needle 632 with the needle 632 extending through the body portion 634. One or more ramp portions 636a, 636b may extend form the disc-shaped body portion 634 to cause the needle carrier 630 to move axially from a first position with the needle 632 retracted beneath the outer surface of the housing base 610 (FIG. 6C) to a second position with the needle 632 advanced beyond the housing base 610 (FIG. 6D) in response to movement of the actuating member(s) 622a, 622b when the syringe 300 is rotated or twisted.

Figure 6A:
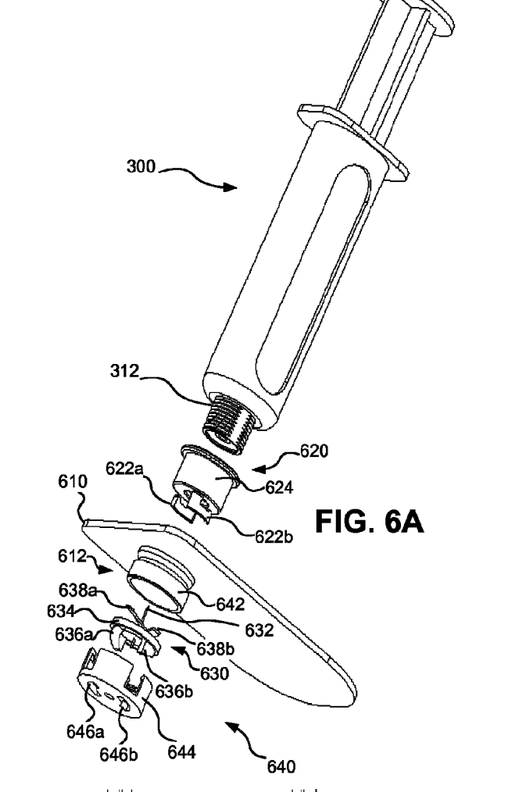
FIG. 6A is an exploded view of a further embodiment of an interface between a prefilled syringe and an infusion pump.
Figure 6B:
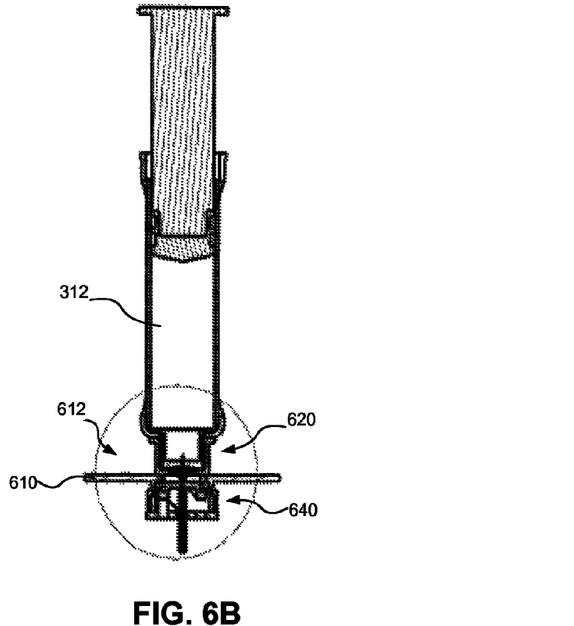
FIG. 6B is a side cross-sectional view of the interface shown in FIG. 6A.
Figure 6C:
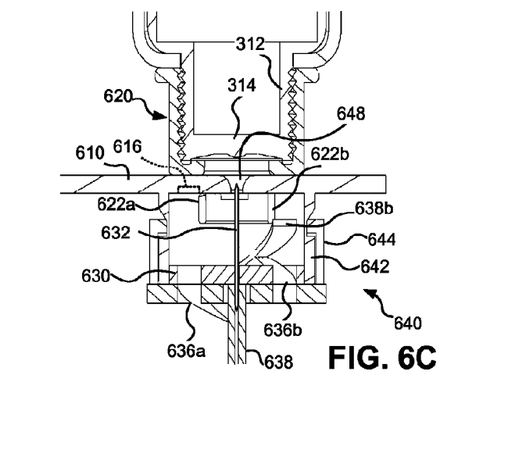
FIG. 6C is an expanded cross-sectional view of the interface shown in FIG. 6B.
Figure 6D:
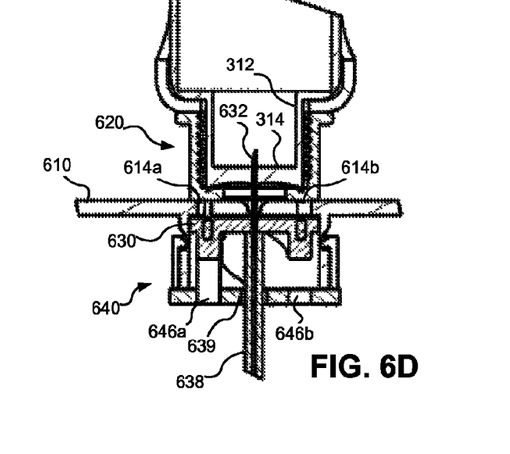
FIG. 6D is an expanded cross-sectional view of the interface shown in FIG. 6B with the prefilled syringe coupled to the pump.
Figure 6E:
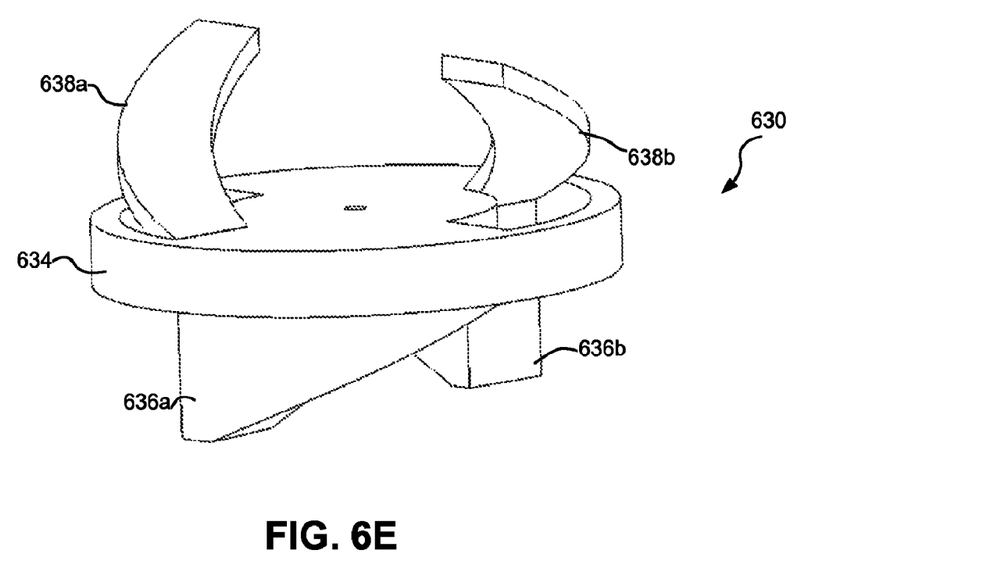
FIG. 6E is a perspective view of a needle carrier used in the interface shown in FIG. 6A.
Figure 6F:
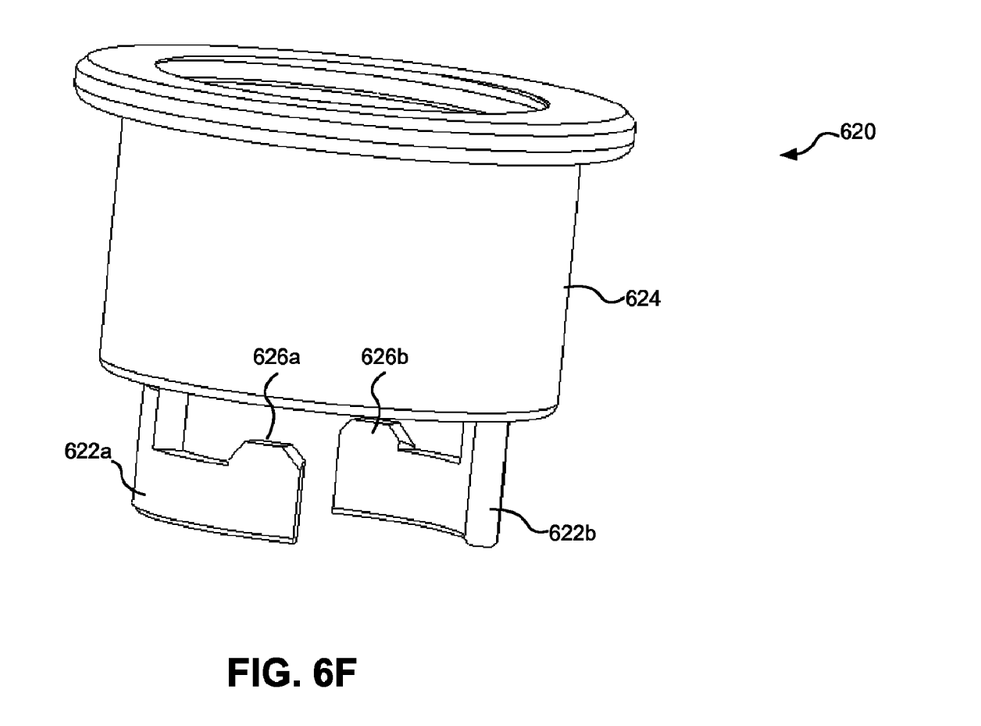
FIG. 6F is a perspective view of a syringe cap used in the interface shown in FIG. 6A.

In one embodiment, one or more portions of the needle carrier 630 are configured to engage the actuating member(s) 622a, 622b such that the rotation of the syringe 300 and the actuating member(s) 622a, 622b causes the needle carrier 630 to rotate. The needle carrier 630 may include, for example, one or more flexible arms 638a, 638b extending from the body portion 634 to engage the actuating member(s) 622a, 622b. The actuating member(s) 622a, 622b may push against the flexible arms 638a, 638b to cause the needle carrier 630 to rotate. The ramp portion(s) 636a, 636b may engage a structure within the recessed portion 640 to cause the needle carrier 630 to move axially when rotated by the actuating member(s) 622a, 622b. The flexible arms 638a, 638b may then fold in when the needle carrier 630 moves axially. When the actuating member(s) 622a, 622b are disengaged and the syringe cap 620 is removed, the flexible arms 638a, 638b may move back to their original position, forcing the needle carrier 630 to withdraw the needle 632.

One embodiment of the recessed portion 640 includes a wall portion 642 and a needle cap 644 that engages the wall portion 642, for example, in a snap fit. The needle carrier 630 is positioned between the needle cap 644 and the housing base 610. The needle cap 644 may include one or more apertures 646a, 646b that receive the ramp portion(s) 634a, 634b of the needle cap when positioned in a first position with the needle 632 retracted (FIG. 6C). When the needle carrier 630 is rotated within the recessed portion 640, the ramp portion(s) 634a, 634b ride up out of the apertures 646a, 646b and onto the cap 644 causing the needle carrier 630 to move axially to the second position with the needle 632 advanced (FIG. 6D). In this second position, the needle passes through a fill port 648 in the housing base 610 and through the needle passage region 314 in the dispensing end 312 of the prefilled syringe 300. The syringe cap 620 may also snap into the second position to indicate that the needle 632 is fully inserted. The actuating members 622a, 622b, for example, may include raised portions 626a, 626b (FIG. 6F) that engage and snap into mating features 616 in the base 610 (FIG. 6C).

A transfer tube 638 may also be coupled to the needle 632 and may extend from the needle carrier 630 to transfer the therapeutic liquid from the needle 632 to a reservoir or to a passageway leading to a reservoir. The transfer tube 638 may pass through an aperture 649 in the needle cap 644 such that the transfer tube 638 moves axially with the needle carrier 630 (FIG. 6D).

Other configurations and mechanisms may also be used to cause the needle carrier 630 to move axially and advance beyond the pump housing base 610 into the dispensing end 312 of the prefilled syringe 300. For example, one or more actuating members may engage one or more ramp portions on the disc shaped body portion such that the ramp portion(s) slide against the actuating member(s) when the actuating member(s) are rotated relative to the needle carrier. According to another configuration, the needle carrier may push the needle up in response to air pressure against the needle carrier, for example, caused by the actuating members engaging the syringe coupling region.

Accordingly, embodiments of the present invention may be used to provide an interface between a prefilled syringe and an infusion pump. Embodiments of the interface may avoid user exposure to the sharp tip(s) of the needle and may ensure proper filling of the infusion pump by providing a secure mechanical engagement between the syringe and the pump housing.

Consistent with one embodiment of the present invention, an infusion pump includes a pump housing comprising a base including a syringe coupling region. The syringe coupling region includes a fill port and at least one recessed engaging portion. The recessed engaging portion is recessed into the pump housing and configured to removably engage a dispensing end of a prefilled syringe or a syringe cap at a dispensing end of a prefilled syringe. A septum covers the fill port and is positioned in the syringe coupling region such that the septum is pierced by a needle in the syringe cap or the dispensing end as the syringe cap or dispensing end engages the recessed engaging portion. A reservoir is located within the housing and fluidly coupled to the syringe coupling region such that the needle is fluidly coupled with the reservoir when the needle passes through the fill port and the septum.

Consistent with another embodiment of the present invention, an infusion pump includes a pump housing comprising a base including a syringe coupling region. The syringe coupling region includes a fill port and a recessed engaging portion recessed into the pump housing and configured to engage a dispensing end of a prefilled syringe. A needle is located in the syringe coupling region and passes through the fill port. The needle is recessed beneath an outer surface of the base and positioned within the recessed engaging portion such that the needle passes through the dispensing end of the prefilled syringe as the dispensing end of the prefilled syringe engages the recessed engaging portion. A reservoir is located within the housing and is fluidly coupled to the needle.

Consistent with a further embodiment of the present invention, an infusion pump includes a pump housing comprising a base including a syringe coupling region. The syringe coupling region includes a fill port and a recessed portion recessed into the pump housing. A needle carrier is located in the recessed portion and configured to move axially within the recessed portion. The needle carrier includes a body portion and a needle extending through the body portion. The needle carrier is configured to move axially from a first position to a second position in response to movement of an actuating member into the syringe coupling region. The needle is recessed beneath an outer surface of the pump housing in the first position and the needle extends outside of the pump housing to pass through the dispensing end of the syringe in the second position. A reservoir is located within the housing and is fluidly coupled to the needle.

Consistent with a further embodiment of the present invention, a syringe cap is provided for coupling a prefilled syringe to an infusion pump. The syringe cap includes a body portion including first and second sides and a syringe coupling portion extending from the body portion on the first side and configured to engage a dispensing end of the prefilled syringe. At least one base engaging member extends from the body portion on the second side and is configured to removably engage at least one recessed engaging portion in a base of an infusion pump. A needle extends through the body portion with a first needle portion of the needle extending from the first side of the body portion and a second needle portion of the needle extending from the second side of the body portion. The first needle portion is configured to pass through the dispensing end of the syringe when the syringe coupling portion is coupled to the syringe. The second needle portion is configured to pass through the base of the infusion pump when the base engaging member is engaged with the base of the infusion pump.

Consistent with yet another embodiment of the present invention, a method is provided includes obtaining a prefilled syringe, the prefilled syringe comprising a prefilled vial containing a predetermined quantity of therapeutic liquid, the prefilled vial having a dispensing end; obtaining an infusion pump comprising a pump housing and a reservoir within the housing, the housing comprising a base including a syringe coupling region, the syringe coupling region including a fill port and a recessed portion recessed into the pump housing; coupling the dispensing end of the prefilled vial to the syringe coupling region of the infusion pump, wherein a needle passes through the base of the pump housing and/or the dispensing end of the prefilled vial when the dispensing end is coupled such that the prefilled vial is fluidly coupled to the reservoir via the fill port; dispensing a predetermined amount of therapeutic liquid from the prefilled vial into the reservoir; and removing the dispensing end of the prefilled vial from the syringe coupling region.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. An infusion pump for interfacing with a prefilled syringe to fill the infusion pump with a therapeutic liquid, the infusion pump comprising:
   a pump housing comprising a base including a syringe coupling region, the syringe coupling region including a fill port and a recessed engaging portion recessed into the pump housing and configured to engage a dispensing end of a prefilled syringe, wherein the recessed engaging portion is internally threaded to engage the dispensing end of the prefilled syringe in a threaded engagement;
   a needle located in the syringe coupling region, the needle having a first end passing through the fill port and a second end, being recessed beneath an outer surface of the base and positioned within the recessed engaging portion such that the second end of the needle passes through the dispensing end of the prefilled syringe as the dispensing end of the prefilled syringe engages the recessed engaging portion; and
   a reservoir located within the housing, the reservoir being fluidly coupled to the needle.

2. The infusion pump of claim 1 further comprising a protective cover positioned in the syringe coupling region, the protective cover being configured to engage the dispensing end of the prefilled syringe such that the protective cover moves from a first position covering the needle to a second position exposing the needle.

3. The infusion pump of claim 2 further comprising a needle shroud positioned around the needle and beneath the protective cover, the needle shroud being configured to move from a first position surrounding the needle to a second position exposing the needle.

4. The infusion pump of claim 1 further including a transfer tube coupled to the needle.

5. A method of filling an infusion pump with therapeutic liquid using a prefilled syringe, the method comprising:
   obtaining a prefilled syringe, the prefilled syringe comprising a prefilled vial containing a predetermined quantity of therapeutic liquid, the prefilled vial having a dispensing end;
   obtaining an infusion pump comprising a pump housing and a reservoir within the housing, the housing comprising a base including a syringe coupling region, the syringe coupling region including a fill port and a recessed portion recessed into the pump housing, wherein a needle is located in the recessed portion of the syringe coupling region, the needle having a first end passing through the fill port and a second end being recessed beneath an outer surface of the base;
   coupling the dispensing end of the prefilled vial to the syringe coupling region of the infusion pump by threadably engaging the recessed portion of the syringe coupling region with the dispensing end such that the needle passes through the dispensing end as the dispensing end is engaged and such that the prefilled vial is fluidly coupled to the reservoir via the fill port;
   dispensing a predetermined amount of therapeutic liquid from the prefilled vial into the reservoir; and
   removing the dispensing end of the prefilled vial from the syringe coupling region.

* * * * *